(12) United States Patent
McMorrow et al.

(10) Patent No.: US 7,901,726 B2
(45) Date of Patent: Mar. 8, 2011

(54) POROUS MEDICAL ARTICLES FOR THERAPEUTIC AGENT DELIVERY

(75) Inventors: David McMorrow, Galway (IE); Anthony Malone, Galway (IE); Tim O'Connor, Galway (IE); Barry J. O'Brien, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 858 days.

(21) Appl. No.: 11/897,808

(22) Filed: Aug. 31, 2007

(65) Prior Publication Data

US 2009/0061071 A1 Mar. 5, 2009

(51) Int. Cl.
*B05D 3/00* (2006.01)
(52) U.S. Cl. ...... 427/2.1; 427/2.24; 427/2.25; 427/430.1
(58) Field of Classification Search ............ 427/2.1
See application file for complete search history.

(56) References Cited

U.S. PATENT DOCUMENTS

| 5,733,925 | A | 3/1998 | Kunz et al. |
| 5,969,020 | A | 10/1999 | Shalaby et al. |
| 2005/0208100 | A1 | 9/2005 | Weber et al. |
| 2006/0051826 | A1 | 3/2006 | Tran-Thi et al. |
| 2006/0127443 | A1 | 6/2006 | Helmus |
| 2006/0129215 | A1 | 6/2006 | Helmus et al. |
| 2006/0153930 | A1 | 7/2006 | Mizushima et al. |
| 2006/0171985 | A1 | 8/2006 | Richard et al. |

FOREIGN PATENT DOCUMENTS

| EP | 1891995 A1 | 2/2008 |
| WO | 2006/103710 | 10/2006 |
| WO | 2007142738 A2 | 12/2007 |

OTHER PUBLICATIONS

Tejal A. Desai et al., "Characterization of Micromachined Silicon Membranes for Immunoisolation and Bioseparation Applications" *J. Membrane Science*, vol. 159 (1999), pp. 221-231.
F. Martin et al., "Tailoring Width of Microfabricated Nanochannels to Solute Size Can Be Used to Control Diffusion Kinetics", *Journal of Controlled Release*, vol. 102 (2005), pp. 123-133.
Rita D'Aquino, "Good Drug Therapy: It's Not Just the Molecule—It's the Delivery", www.cepmagazine.org., Feb. 2004 CEP, pp. 15S-17S.

*Primary Examiner* — Michael Barr
*Assistant Examiner* — Andrew Bowman
(74) *Attorney, Agent, or Firm* — Mayer & Williams PC; David B. Bonham; Keum J. Park

(57) ABSTRACT

According to an aspect of the present invention a method is provided which a porous medical article is contacted with a solution that contains a therapeutic agent and a solvent in order to load the pores of the medical article, after which the solvent is sublimated.

21 Claims, 4 Drawing Sheets

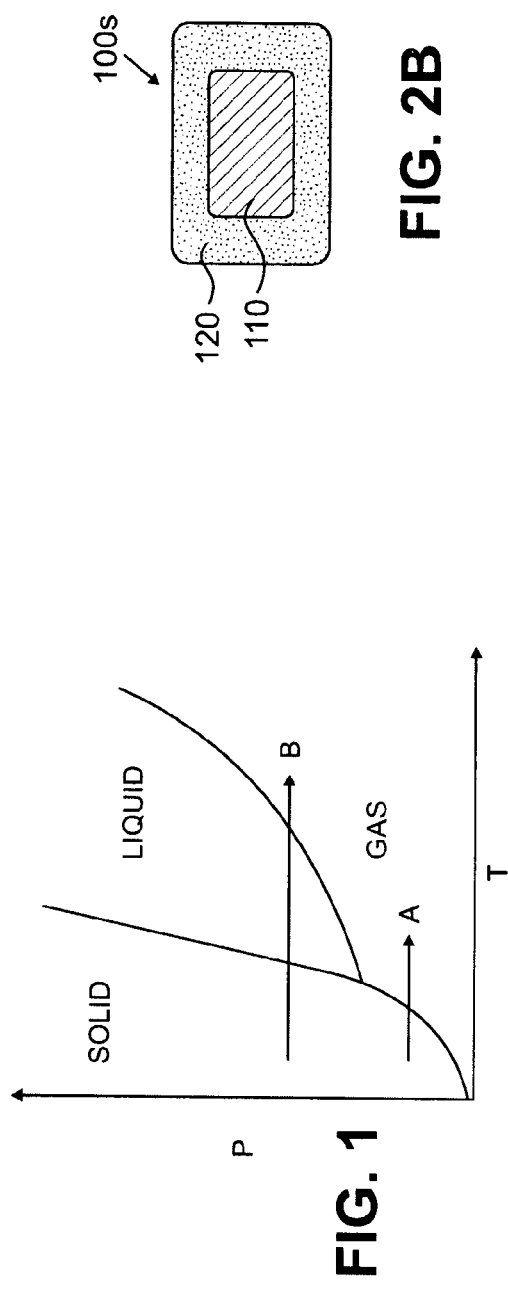
FIG. 1
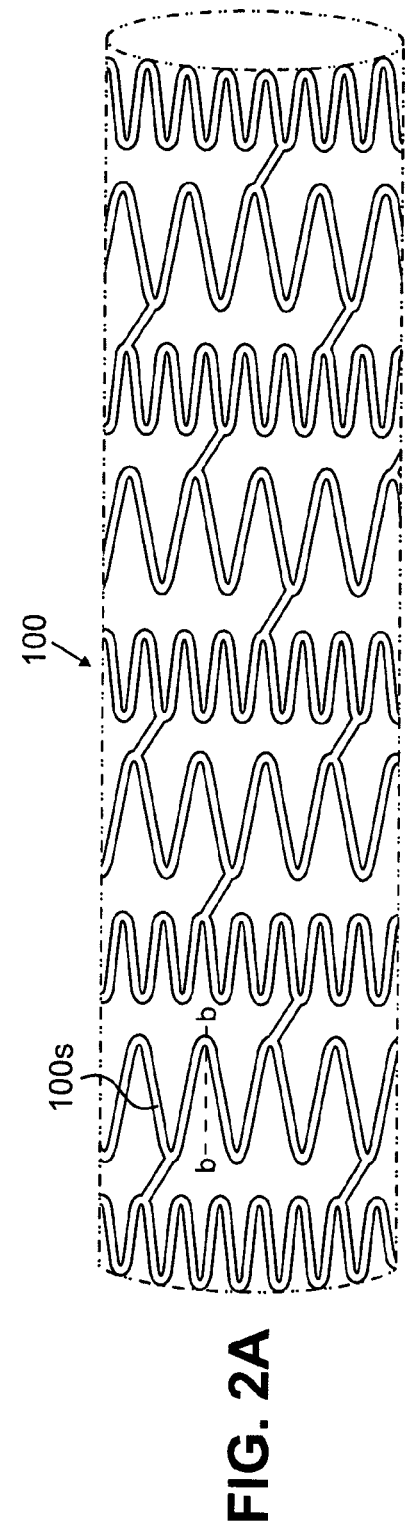
FIG. 2A
FIG. 2B

POROUS MEDICAL ARTICLES FOR THERAPEUTIC AGENT DELIVERY

TECHNICAL FIELD

This invention relates to therapeutic-agent-containing medical articles, and more particularly, to medical articles having porous regions from which therapeutic agent is released.

BACKGROUND OF THE INVENTION

The in-situ delivery of therapeutic agents within the body of a patient is common in the practice of modern medicine. In-situ delivery of therapeutic agents is often implemented using medical articles that may be temporarily or permanently placed at a target site within the body. These medical articles can be maintained, as required, at their target sites for short or prolonged periods of time, in order to deliver therapeutic agents to the target site.

For example, in recent years, drug eluting coronary stents, which are commercially available from Boston Scientific Corp. (TAXUS), Johnson & Johnson (CYPHER) and others, have become the standard of care for maintaining vessel patency after balloon angioplasty. These existing products are based on metallic balloon expandable stents with biostable polymer coatings, which release antiproliferative drugs at a controlled rate and total dose.

Nanoporous materials have the potential to revolutionize drug delivery. For example, iMEDD, Inc. has created silicon membranes with parallel channels ranging from 4 to 50 nm. Diffusion rates of various solutes through such membranes have been measured and conform to zero-order kinetics in some instances (i.e., release is constant with time). This is in contrast with typical situations in which drug diffusion rates decay with time, because the concentration gradient, and thus the driving force for diffusion, is also decaying with time. Diffusion is ordinarily governed by Fick's law, which states that the flux of a given substance (i.e., the amount of the substance crossings unit area per unit time) arising from molecular diffusion is directly proportional to the concentration gradient of the substance. One explanation for zero order behavior is that, by making the diameter of the nanopores only slightly larger than that of the drug, the nanopores act as bottlenecks, forcing the drugs to proceed in a substantially single-file fashion through the membrane. iMedd claims that the membranes can be engineered to control rates of diffusion by adjusting channel width in relation to the size of solutes. When the proper balance is struck, zero-order diffusion kinetics is possible. iMedd has produced a drug delivery device which consists of a drug-filled enclosure which is fitted with a nanoporous membrane as the only connection between the internal reservoir of the device and the external medium.

SUMMARY OF THE INVENTION

According to an aspect of the present invention, a method is provided in which a porous medical article is contacted with a solution that contains a therapeutic agent and a solvent in order to load the pores of the medical article, after which the solvent is sublimated.

In certain embodiments, porous medical articles are loaded with therapeutic agents by a method that comprises (a) contacting a medical article with a solution comprising a therapeutic agent and a first solvent such that pores of the medical article are at least partially filled with the solution, (b) cooling the medical article to a temperature that is below the freezing point of the solution, (c) washing the medical article in a second solvent at a temperature below the freezing point of the solution and above the freezing point of the second solvent, and (d) sublimating the first solvent.

Advantages of the present invention may include one or more of the following:

(a) enhanced total therapeutic agent payload that can be loaded into the medical article,
(b) reduced amount of therapeutic agent on the external surface of the medical article, and
(c) reduced residual solvent trapped in the pores of the medical article.

These and other embodiments and advantages of the present invention will become immediately apparent to those of ordinary skill in the art upon review of the Detailed Description and Claims to follow.

BRIEF DESCRIPTION OF THE DRAWINGS

FIG. 1 is a generalized schematic phase diagram.
FIG. 2A is a schematic perspective view of a coronary stent, in accordance with an embodiment of the invention.
FIG. 2B is an expanded schematic cross-sectional view taken along line b-b of FIG. 2A.

DETAILED DESCRIPTION

Figure 3:
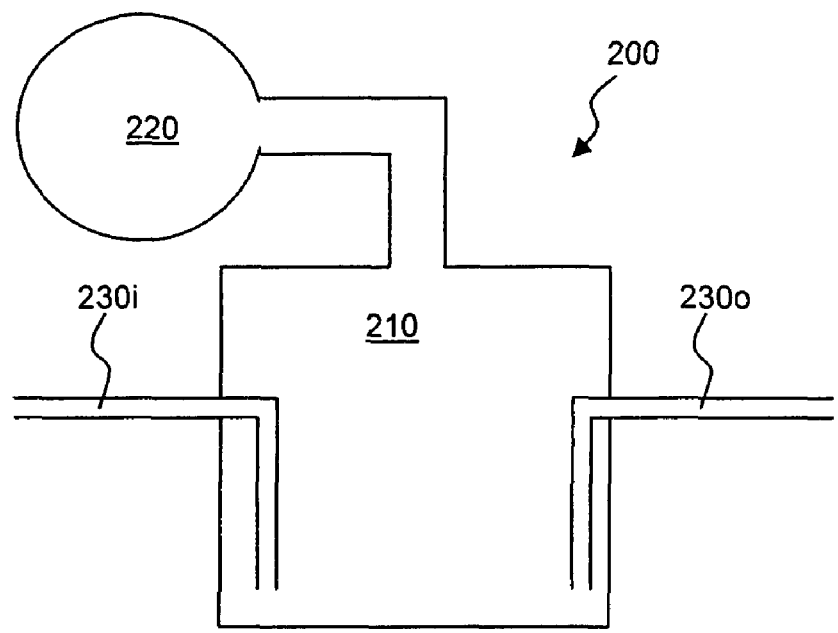
FIG. 3 is a schematic view of an apparatus for processing a medical device in accordance with the present invention.

The present invention is directed to processes for loading medical articles having porous surfaces with therapeutic agents.

"Therapeutic agents," "biologically active agents," "drugs," "pharmaceutically active agents," "pharmaceutically active materials," and other related terms may be used interchangeably herein. A wide variety of therapeutic agents can be employed in conjunction with the present invention including those used for the treatment of a wide variety of diseases and conditions. As used herein, "treatment" refers to the prevention of a disease or condition, the reduction or elimination of symptoms associated with a disease or condition, or the substantial or complete elimination of a disease or condition. Subjects are vertebrate subjects, more typically mammalian subjects including human subjects, pets and livestock.

A porous surface is one that comprises pores. Medical articles having a wide variety of pore sizes may be loaded in accordance with the present invention. Pore sizes may range, for example, from nanopores (i.e., pores having widths of 50 nm or less), including micropores (i.e., pores having widths smaller than 2 nm) and mesopores (i.e., pores having a widths ranging from 2 to 50 nm), to macropores (i.e., pores having widths that are larger than 50 nm). As used herein, a nanoporous surface is one that comprises nanopores (commonly at least $10^6$, $10^9$, $10^{12}$ or more nanopores per $cm^2$), a microporous surface is one that comprises micropores, a mesoporous surface is one that comprises mesopores, and a macroporous surface is one that comprises macropores.

The present invention is applicable to a broad range of medical articles with porous surfaces. Medical articles for use in conjunction with the present invention include, for example, controlled drug delivery articles and devices that are implanted or inserted into the body, for example, for procedural uses or as implants. Examples of medical devices include, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, balloons (e.g., balloons with porous coatings), filters (e.g., vena cava filters and mesh filters for distil protection devices), embolization devices including cerebral aneurysm filler coils (including Guglilmi detachable coils and metal coils), septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body and from which therapeutic agent is released.

Thus, while the medical articles of the invention in some embodiments may simply provide for controlled release of one or more therapeutic agents as a dosage form, in other embodiments, the medical articles of the invention are configured to provide a therapeutic function beyond controlled species transport, for instance, providing mechanical, thermal, magnetic and/or electrical functions within the body, among other possible functions.

The medical articles of the present invention include, for example, implantable and insertable medical articles that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

The medical articles which may be loaded with therapeutic agents in accordance with the present invention have porous surface regions, which may correspond to the entire surface of the article or to only a portion (or portions) of the article surface. Medical articles for use in the invention thus include those which are porous throughout, those in which a porous layer is provided over an underlying substrate, and so forth.

Thus, one or more porous surface-regions can be provided on the medical article surface at desired locations and/or in desired shapes (e.g., in desired patterns). For example, for tubular devices such as stents (which can comprise, for example, a laser or mechanically cut tube, one or more braided, woven, or knitted filaments, etc), the porous surface regions can be present on the inner (luminal) surface, on the outer (abluminal) surface, on the lateral surfaces between the luminal and abluminal surfaces, patterned along the luminal or abluminal length of the device, on the ends, and so forth. Moreover, multiple porous surface regions having the same or different therapeutic agents can be provided, for instance, using appropriate masking techniques. As an example, it is possible to provide a tubular medical article (e.g., a vascular stent) having a first nanoporous region comprising a first biologically active agent (e.g., an antithrombotic agent) on its inner luminal, surface and a second nanoporous region comprising a second biologically active agent that differs from the first biologically active agent (e.g., an antiproliferative agent) on its outer, abluminal surface.

Many techniques are known by which porous regions, including nanoporous and macroporous regions, may be formed for use in conjunction with medical articles, for instance, porous regions corresponding to an entire article or article component, to a porous coating on an underlying substrate, and so forth. As previously indicated, pore sizes may range, for example, from pores on the order of 1 nm (e.g., for zeolites of aluminum oxides) to pores on the order of 1 μm (e.g. for sol-gel materials) or larger. For further information regarding the formation of medical devices with porous regions, see, e.g., Pub. Nos. US 2005/0208100, US 2006/0129215, US 2006/0127443, US 2006/0171985 and the references therein.

Materials for forming porous regions, as well as underlying substrates in some cases, may vary widely in composition and are not limited to any particular material. They can be selected from a range of biostable materials and biodisintegrable materials (i.e., materials that are dissolved, degraded, resorbed, or otherwise eliminated upon placement in the body), including (a) organic materials (i.e., materials containing organic species, typically 50 wt % or more) such as polymeric materials (i.e., materials containing polymers, typically 50 wt % or more polymers) and biologics, (b) inorganic materials (i.e., materials containing inorganic species, typically 50 wt % or more), such as metallic materials (i.e., materials containing metals, typically 50 wt % or more) and non-metallic inorganic materials (e.g., including carbon, semiconductors, glasses and ceramics, which may contain various metal-and non-metal-oxides, various metal-and non-metal-nitrides, various metal-and non-metal-carbides, various metal-and non-metal-borides, various metal-and non-metal-phosphates, and various metal-and non-metal-sulfides, among others), and (c) hybrid materials (e.g., hybrid organic-inorganic materials, for instance, polymer/metallic inorganic and polymer/non-metallic inorganic hybrids).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals such as gold, iron, niobium, platinum, palladium, iridium, osmium, rhodium, titanium, tantalum, tungsten, ruthenium, and magnesium, among others, and alloys such as those comprising iron and chromium (e.g., stainless steels, including platinum-enriched radiopaque stainless steel), niobium alloys, titanium alloys including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium and/or iron (and their alloys with combinations of Ce, Ca, Zn, Zr and Li), among others.

Specific examples of organic materials include polymers, which may be biostable or biodegradable, natural or synthetic, crosslinked or thermoplastic, as well as other high molecular weight organic materials.

Depending on the pore size and the size of the therapeutic agent, it is known that nanoporous layers having parallel or near parallel pore structures can release species such as therapeutic agents in accordance with zero order kinetics. In some instances, the lateral dimensions (e.g., the radii) of the interconnected pores approach the lateral dimensions (e.g., the hydrated radius) of the species that is being transported. Consequently, the species may move within, and ultimately be released from, pores of these diameters (as opposed to being trapped by pores having smaller diameters). Under such circumstances, the interactions between the species and the walls of the nanopores will have a significant effect upon the transport that is observed. Indeed, as the diameter of the pore approaches the diameter of the species that is being transported, the surface interactions begin to dominate transport. See, e.g., Tejal A. Desai, Derek Hansford and Mauro Ferrari, "Characterization of micromachined silicon membranes for immunoisolation and bioseparation applications" *J. Membrane Science,* 159 (1999) 221-231, which describes insulin release through silicon nanomembranes. See also F. Martin et al., *Journal of Controlled Release,* 102 (2005) 123-133, in which diffusion kinetics of various solutes were measured across silicon-based membranes having arrays of uniform channels. Non-Fickian behavior was observed as channel width approached the hydrodynamic diameter of the solute. (As noted above, molecular diffusion is ordinarily governed by Fick's law—when this law is not followed, the behavior is deemed "non-Fickian.") Zero-order diffusion, which is clearly non-Fickian, was observed at a channel width of 20 nm for interferon, and the same phenomenon was observed with albumin (BSA) at a channel width of 13 nm.

In other less-structured nanoporous layers, the species may travel through the region via interconnected networks of pores. As with parallel pore structures, interconnected pore structures are capable of transporting species in a highly controlled manner, and they have the potential to approach zero order transport kinetics where pore diameters approach the size of the species that is being transported. The transport rate may also be affected by the tortuousity of the interconnected pores and the thickness of the layer, among other factors.

In loading therapeutic agents into porous regions of medical articles via surface pores, it is frequently preferred that the porous regions be filled with therapeutic agent to the greatest extent possible. This enables the therapeutic agent payload for a given medical article to be maximized, for instance, enabling the volume of a porous layer on an underlying substrate (e.g., the thickness) to the minimized. For example, in the case of a stent, this allows for smaller strut dimensions.

In order to maximize therapeutic agent loading, the present invention utilizes a process in which a porous medical article is contacted with a solution that contains a therapeutic agent and a solvent in order to load the pores of the medical article, after which the solvent is sublimated (e.g., via a freeze-drying process).

In this regard, the initial solution may be loaded into the pores of the medical article via one or more mechanisms, including natural capillary forces, pressure-assisted loading and vacuum-assisted loading, among others. For example, a medical article may be inserted into a vacuum chamber under vacuum followed by contact of the initial solution with the article under pressure such that it is forced into the evacuated porous region, or a medical article may be inserted into the initial solution under vacuum conditions and the pressure increased.

Sublimation of the solvent leaves behind precipitated/crystallized therapeutic agent within the pores. A solvent removal step ordinarily presents various practical difficulties, including, for example, the fact that residual solvent may remain trapped in the pores. The use of a sublimation step, however, overcomes such difficulties.

"Sublimation" is conversion of a material (in the present invention, a solvent) from a solid state (also referred to herein as a "frozen" state) to a gas state (also referred to herein as a "vapor" state) without first going through a liquid state. For many materials, including a variety of solvents, sublimation may be achieved by increasing the temperature of the material in its solid state while operating at low pressure. This can be seen by referring to arrow A in the generalized schematic phase diagram illustrated in FIG. 1. Note that raising the temperature of the solid material at a higher pressure, as illustrated by arrow B, will result in the material passing through the liquid state before reaching the gas state. The actual pressure that is required varies from material to material, and can be determined, for example, by examining the phase diagram for the material of interest.

Sublimation from a solid state, rather than evaporation from a liquid state, when removing a solvent from a porous region, offers several advantages. First, because the frozen solvent within the pores is converted directly from a solid to a gas, no flow of liquid solvent occurs, which could cause an undesirable transfer of therapeutic agent back out of the pores. Second, when the solution is frozen in the pores, a washing process may be carried out to remove excess therapeutic agent on the outer surface.

In this regard, and in accordance with an embodiment of the invention, a method of loading a porous medical article is provided, which comprises (a) contacting the medical article with a solution comprising a therapeutic agent and a first solvent (e.g., to introduce the solution into the pores of the article), (b) cooling the medical article to a temperature that is below the freezing point of the solution, (c) washing the medical article in a second solvent at a temperature below the freezing point of the solution and above the freezing point of the second solvent (e.g., to remove the frozen solution from the surface of the article), and (d) sublimating the first solvent.

The first and second solvents may be selected based on one or more of the following criteria, among others. (1) To maximize the amount of therapeutic agent loading, the solubility of the therapeutic agent in the first solvent is preferably maximized. (2) The phase behavior of the first solvent should be such that first solvent can be sublimed at a suitable pressure and temperature range (e.g., in a suitable apparatus such as a freeze drying apparatus). (3) In order to wash the medical article with the second solvent at a temperature below the freezing point of the solution, the second solvent must have a freezing point below the freezing point of the solution. (4) In order to remove the frozen solution from the surface of the medical article, the second solvent may be a reasonably good solvent for any first solvent that is present on the surface, which will be in a solid state. If the first solvent does not display good solubility in the second solvent when the first solvent is in the solid state, then therapeutic agent contained within the frozen solution would not be affected and only discrete crystals on the outside of the medical article are available for dissolution. The therapeutic agent may be soluble or insoluble in the second solvent. Either approach may be used, but the results may depend on the efficiency of the washing/cleaning process. The washing process may be enhanced by using jets of solvent, ultrasonic energy, physical removal (e.g., wiping), and so forth. For example, a wiping method may be used in conjunction with a second solvent that is not a good solvent for the therapeutic agent, as any discrete therapeutic agent crystals on the outside of the article can wiped off. In other embodiments, the therapeutic agent is slightly less soluble in the second solvent than in the first solvent, but not insoluble. Having slightly less solubility ensures that other parameters such as time, temperature, agitation, and so forth, can be used to control the washing process. Even where both components of the initial solution (therapeutic agent and first solvent) have good solubility in the second solvent, these components remain relatively protected within the pores, for example, because relatively little surface area is exposed to the second solvent and, because the mobilities of the components of the initial solution are very low (due to the fact that the solution is frozen).

Solvent species that can be used in connection with the present invention may be selected, for example, from suitable members of the following: (a) water, (b) alkanes such as ethane, hexane, octane, cyclohexane, heptane, isohexane, butane, pentane, isopentane, 2,2,4-trimethlypentane, nonane, decane, dodecane, hexadecane, eicosane, methylcyclohexane, cis-decahydronaphthalene and trans-decahydronaphthalene, (c) aromatic species such as benzene, toluene, xylene(s), naphthalene, styrene, ethylbenzene, 1-methylnaphthalene, 1,3,5-trimethylbenzene, tetrahydronaphthalene, diphenyl and 1,4-diethylbenzene, (d) halohydrocarbons including (i) chlorohyhdrocarbons such as chloroform, methyl chloride, dichloromethane, 1,1-dichloroethylene, ethylene dichloride, ethylidene chloride, propyl chloride, cyclohexyl chloride, 1,1,1-trichloroethane, perchloroethylene, trichloroethylene, butyl chloride, carbon tetrachloride, tetrachloroethylene, chlorobenzene, o-dichlorobenzene, benzyl chloride, trichlorobiphenyl, methylcyclohexane, 1,1,2,2-tetrachloroethane (ii) fluorinated halogenated species such as chlorodiflouoromethane, dichlorofluoromethane, dichlorodifluoromethane, trichlorofluoromethane, 1,2-dichlorotetrafluoroethane, 1,1,2-trichlorotrifluoroethane, perfluor (methylcyclohexane), perfluor(dimethylcyclohexane) and (iii) other halohydrocarbons such as ethyl bromide, ethylidene bromide, ethylene dibromide, tribromomethane, bromotrifluoromethane, 1,1,2,2-tetrabromoethane, bromobenzene, bromochloromethane, 1-bromonaphthalene, methyl iodide, methylene diiodide (e) acid aldehydes/anhydrides such as acetaldehyde, furfural, butyraldehyde, benzaldehyde, acetyl chloride, succinic anhydride and acetic anhydride, (f) alcohols including (i) phenols such as phenol, 1,3-benzenediol, m-cresol, o-methoxyphenol, methyl salicylate and nonylphenol, (ii) polyhydric alcohols such as ethylene glycol, glycerol, propylene glycol, 1,3-butanediol, diethylene glycol, triethylene glycol, hexylene glycol and dipropylene glycol, and (iii) other alcohols such as methanol, ethanol, ethylene cyanohydrin, allyl alcohol, 1-propanol, 2-propanol, 3-chloropropanol, furfuryl alcohol, 1-butanol, 2-butanol, benzyl alcohol, isobutanol, cyclohexanol, 1-pentanol, 2-ethyl-i-butanol, diacetone alcohol, 1,3-dimethyl-1-butanol, ethyl lactate, butyl lactate, ethylene glycol monomethyl ether, ethylene glycol monoethyl ether, diethylene glycol monomethyl ether, diethylene glycol monoethyl ether, ethylene glycol monobutyl ether, 2-ethyl-1-hexanol, 1-octanol, 2-octanol, diethylene glycol monobutyl ether, 1-decanol, 1-tridecyl alcohol, nonyl-phenoxy ethanol, oleyl alcohol, triethylene glycol mono-oleyl ether, (g) ethers such as, epichlorohydrin, furan, 1,4-dioxane, dimethoxymethane, diethyl ether, bis-(2-chloroethyl) ether, anisole, di-(2-methoxyethyl) ether, dibenzyl ether, di-(2-chloroisopropyl) ether, bis-(m-phenoxyphenol) ether, dimethyl ether and tetrahydrofuran, (h) ketones, such as acetone, cylohexanone, isophorone, diethyl ketone, mesityl oxide, acetophenone, methyl ethyl ketone, methyl isoamyl ketone, methyl isobutyl ketone, and methyl propyl ketone, (i) acids such as formic acid, acetic acid, benzoic acid, butyric acid, octanoic acid, oleic acid, stearic acid, (j) esters/acetates such as ethylene carbonate, butyrolactone, propylene-1,2-carbonate, ethyl chloroformate, ethyl acetate, trimethyl phosphate, diethyl carbonate, diethyl sulfate, ethyl formate, methyl acetate, n-butyl acetate, isobutyl acetate, t-butyl acetate, 2-ethoxyethyl acetate, isoamyl acetate, dimethyl phthalate, ethyl cinnamate, triethyl phosphate, diethyl phosphate, butyl benzyl phthalate, dibutyl phthalate, diethyl phthalate, tricrysyl phosphate, tributyl phosphate, dibutyl sebacate, methyl oleate, dioctyl phthalate, dibutyl stearate isopropyl acetate, isobutyl isobutyrate, n-propyl acetate and n-butyl propionate, (k) nitrogen compounds such as acetonitrile, acrylonitrile, propionitrile, butyronitrile, nitromethane, nitroethane, 2-nitropropane, nitrobenzene, ethanolamine, ethylenediamine, 1,1-dimethylhydrazine, 2-pyrrolidone, pyridine, propylamine, morpholine, analine, n-methyl-2-pyrrolidone, butylamine, diethylamine, cyclohexylamine, quinoline, dipropylamine, formamide, n,n-dimethylformamide, n,n-dimethylacetamide, tetramethylurea, hexamethyl phosphoramide, diethylenetriamine, triethylamine and triethanolamine, and (l) sulfur compounds such as carbon disulfide, dimethylsulfoxide, ethanethiol, dimethyl sulfone and diethyl sulfide.

A specific embodiment of the invention will now be described with reference to the drawings. Although this embodiment is directed to a stent, the invention is clearly applicable to other medical articles as previously indicated.

In the field of drug-eluting stents, it is desirable in some instances to deliver a therapeutic agent without the use of polymer excipients. (Polymer excipients are used to deliver therapeutic agents from commercially available stents such as TAXUS and CYPHER, among others.) For example, a metallic stent may be provided with a porous inorganic coating, for instance, a nanoporous coating of carbon, a metal oxide or a semi-metal oxide, among other possibilities (see above). Few technologies are known, however, which can efficiently load nanoporous coatings with therapeutic agents. The present invention provides such a method.

Turning now to FIG. 2A, a schematic perspective view of a vascular stent 100 in accordance with an embodiment of the invention is shown. Stent 100 contains various stent struts 100s, as is known in the vascular stent art. FIG. 2B is an expanded schematic cross-sectional view taken along line b-b of FIG. 2A and illustrates a stent substrate 110 (e.g., a stainless steel or nitinol substrate, etc.), and a nanoporous layer 120 (e.g., a nanoporous coating of carbon, a metal oxide, a semi-metal oxide, etc.) provided over the stent substrate 110. The nanoporous layer 120 is loaded with therapeutic agents in accordance with the present invention, and thus has, for example, minimal residual solvent trapped in its pores, enhanced therapeutic agent loading in its pores, and minimal therapeutic agent on its surface.

A specific embodiment of the invention will now be described with reference to FIGS. 3 and 4A-4D. FIG. 3 is a schematic illustration of an apparatus 200 that may be used to carry out various methods in accordance with the invention and includes a central chamber 210, a pressure regulating component 220 capable of establishing sub-ambient (vacuum) and supra-ambient (elevated) pressure conditions in the chamber 210. The apparatus 200 further includes an inlet 230i and an outlet 230o by which solvent may be introduced into and removed from the chamber 210.

Figure 4A:
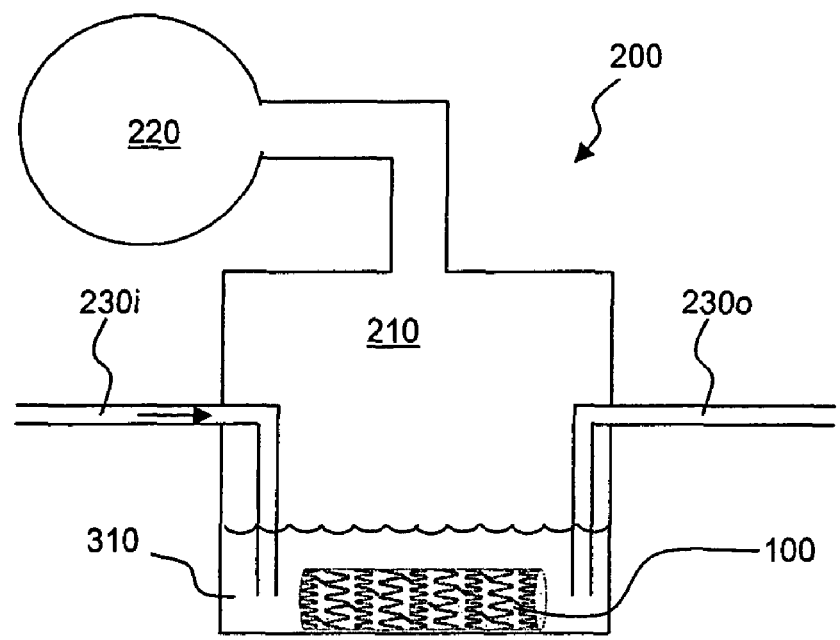
FIGS. 4A-4D are schematic illustrations showing a process, in accordance with an embodiment of the present invention, which uses the apparatus of FIG. 3.

Turning to FIG. 4A, a nanoporous stent 100 (e.g. a metallic stent with a nanoporous coating) is immersed in a solution 310, which may be introduced, for example, via inlet 230i. The solution 310 in this particular embodiment contains a therapeutic agent, such as paclitaxel, and a first solvent, such as toluene. Paclitaxel concentration may be at or near saturation (e.g., 90% or more) in this embodiment. The solution 310 and stent 100 may be introduced to one another, for example, under vacuum conditions. Loading may be assisted in this embodiment by pressurizing the chamber 210 to ambient or super-ambient pressure to push the solution into pores of the stent 100. In some embodiments, the solvent may be heated to increase the amount of therapeutic agent that can be dissolved in the first solvent.

Figure 4B:
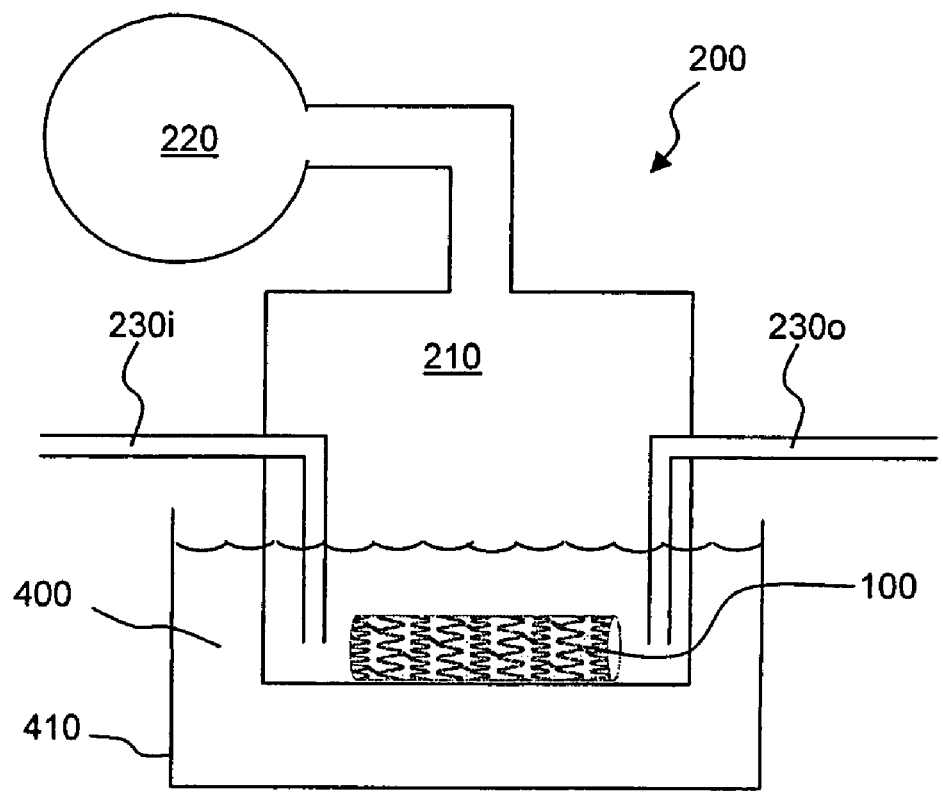

Excess solution is then drained and the remaining solution 310 (including that present in the pores) is frozen, for example, by immersion into a container 410 of liquid nitrogen 400 as shown in FIG. 4B, among other possibilities. At the time of freezing, the exterior of the stent 100 may be wet with the solution 310 (or may even be immersed in the solution 310). Pressure may be maintained at an elevated level during this step, if desired.

As an optional step, the first solvent may be subjected to sublimation at this point, followed by a repeat of the above steps (contact of the stent with the solution, followed by freezing). One may preferably control process parameters such as time, pressure and temperature to ensure that the initially deposited material is not re-dissolved to any significant degree in latter steps, which could reduce the benefit of the repeated steps. For instance, the extent and duration of contact between the initially deposited material and the subsequently loaded solution are preferably minimized.

As an alternative optional step, the first solvent may be subjected to sublimation at this point, followed by a repeat of the above steps (contact of the stent with the solution, followed by freezing) using a solution that contains a different therapeutic agent. The solvent used may be the same or different from the first solvent. Where a different solvent is employed, the solvent selected may be a poor solvent for the initially applied therapeutic agent and a good solvent for the different therapeutic agent. In these embodiments, the different solvent will have a freezing point that is above that of the second solvent, allowing the washing the medical article in the second solvent at a temperature below the freezing point of the solution containing the different therapeutic agent and above the freezing point of the second solvent (e.g., to remove the frozen solution from the surface of the article). In this way, pores may be provided with discrete layers of different drugs. (As an alternative, before application of the different drug, all of the steps described here, including those described in FIGS. 4C and 4D below, may first be followed, followed by a repeat of the various steps of the invention with the different drug, using suitable solvents selected according to the guidelines set forth herein.)

Figure 4C:
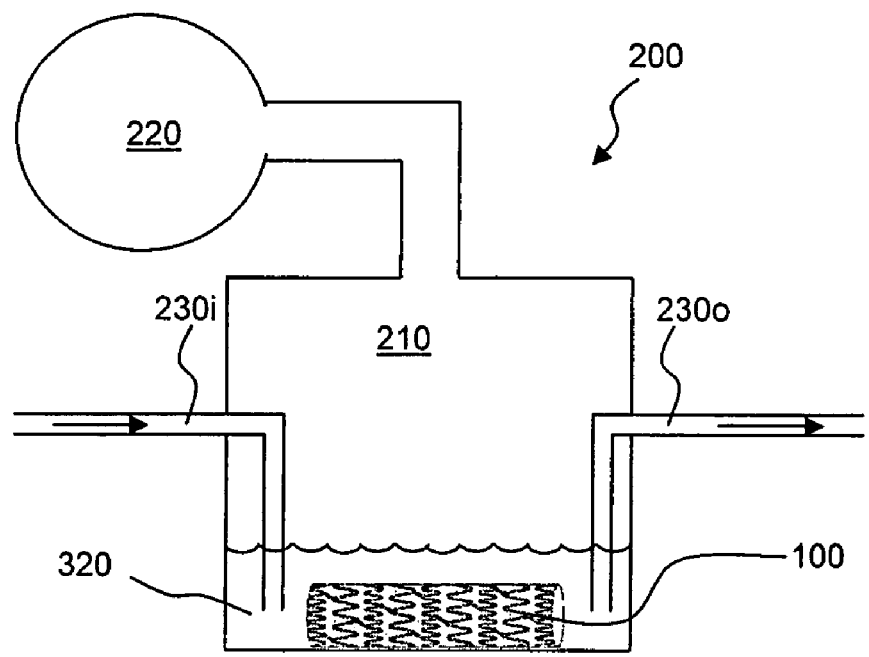

As shown in FIG. 4C, the stent 100 is then washed with a second solvent 320 at a temperature that is lower than the freezing point of the frozen solution 310, but higher than the freezing point of the second solvent. For example, the second solvent can be introduced into the chamber via inlet 230i and removed from the chamber via outlet 230o, and the chamber pressure may be adjusted as needed to control evaporation, for instance, depending on solvent choice (e.g., the chamber pressure may be adjusted to at or around atmospheric pressure, to elevated pressures, or to reduced pressures, as desired). For this step, the second solvent 320 is selected to have a freezing point that is lower than that of the first solvent. In this example, the second solvent 320 is isopropanol, although other solvents are possible. Exposure of the stent 100 to the second solvent acts to wash therapeutic agent and frozen first solvent from the surface of the stent 100 (e.g., by dissolution), while the therapeutic agent and frozen first solvent within the pores are substantially protected from the effects of the second solvent, as discussed above. Even though the first solvent on the surface of the stent is in a solid state, it is nonetheless soluble in the second solvent, so the first solvent is removed from the surface by dissolution in the second solvent.

Figure 4D:
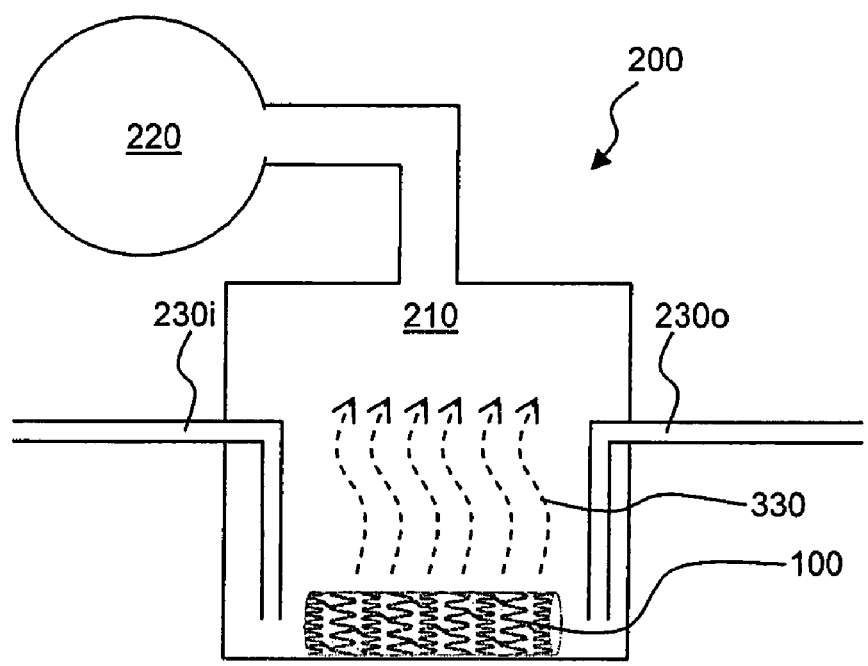

In a final step, the pressure is decreased (e.g., to vacuum conditions) and the temperature is increased, resulting in the sublimation of the first solvent (e.g., remaining within the pores) to the vapor phase 330 as illustrated schematically in FIG. 4D. This results in crystallization/precipitation of the paclitaxel within the pores, where it remains. The second solvent may evaporate or sublimate, depending on its phase diagram and on the processing parameters selected.

Therapeutic agents may be loaded in accordance with the present invention for any number of purposes, for example, to affect tissue adhesion vis-à-vis the medical article, to influence thromboresistance, to influence antihyperplastic behavior, to enhance recellularizaton, or to promote tissue neogenesis, to influence antihyperplastic behavior, among many other purposes.

Suitable non-genetic therapeutic agents for use in connection with the present invention may be selected, for example, from one or more of the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/ antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o)agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.).

Preferred non-genetic therapeutic agents include paclitaxel (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor a and 0, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., PCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular and other treatment regimens, for example, as agents targeting restenosis. Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E-and P-selectins, (q) inhibitors of VCAM-1 and ICAM-1 interactions, (r) prostaglandins and analogs thereof including prostaglandins such as PGE1 and PG12 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 to Kunz et al.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method of loading a porous medical article comprising (a) contacting a medical article with a therapeutic-agent-containing solution that comprises a therapeutic agent and a first solvent such that pores of the medical article are at least partially filled with the solution, (b) cooling the medical article to a temperature that is below the freezing point of the solution, (c) washing the medical article in a second solvent at a temperature below the freezing point of the solution and above the freezing point of the second solvent, and (d) removing the first solvent by sublimation.

2. The method of claim 1, wherein the medical article is submerged in the therapeutic-agent-containing solution and the pressure is subsequently increased.

3. The method of claim 1, wherein the first solvent is removed by sublimation under vacuum conditions.

4. The method of claim 1, wherein the first solvent is removed by freeze drying.

5. The method of claim 1, wherein the therapeutic agent is present in the solution at 90% or more of the saturated concentration.

6. The method of claim 1, wherein the solution is heated to increase the solubility of the therapeutic agent.

7. The method of claim 1, wherein the wherein the therapeutic agent is selected from paclitaxel, everolimus, sirolimus and their analogs and derivatives.

8. The method of claim 7, wherein the first solvent is selected from toluene, tetrahydrofuran and ethanol.

9. The method of claim 7, wherein the first solvent is toluene and the second solvent is isopropanol.

10. The method of claim 7, wherein the medical article is selected from a stent with a porous coating and a balloon with a porous coating.

11. The method of claim 1, wherein the medical article is a nanoporous medical article.

12. The method of claim 1, wherein the medical article is a mesoporous medical article.

13. The method of claim 1, wherein the medical article produced exhibits non-Fickian release kinetics.

14. The method of claim 1, wherein the medical article comprises a substrate and a porous layer disposed over the substrate.

15. The method of claim 14, wherein the substrate is a metallic substrate and the porous layer is an inorganic porous layer.

16. The method of claim 1, wherein the medical article is an insertable medical device.

17. The method of claim 16, wherein the insertable medical device is a balloon with a porous outer coating.

18. The method of claim 1, wherein the medical article is an implantable medical device.

19. The method of claim 17, wherein the implantable medical device is a stent.

20. The method of claim 1, wherein the therapeutic agent is an antiproliferative agent.

21. The method of claim 1, wherein the first and second solvents are organic solvents.

* * * * *